United States Patent [19]

Alt

[11] Patent Number: 4,600,433

[45] Date of Patent: Jul. 15, 1986

[54] HERBICIDAL 2-HALOACETAMIDES

[75] Inventor: Gerhard H. Alt, University City, Mo.

[73] Assignee: Monsanto Company, St. Louis, Mo.

[21] Appl. No.: 133,760

[22] Filed: Mar. 25, 1980

[51] Int. Cl.[4] ............ A01N 37/18; A01N 43/08; C07D 307/54; C07D 209/34
[52] U.S. Cl. ............................ 71/118; 71/88; 549/496; 564/212
[58] Field of Search ............ 71/118, 88; 260/562, 260/347.3; 564/212; 549/496

[56] References Cited

U.S. PATENT DOCUMENTS 3,574,746  4/1971  Chupp .................... 71/118
3,586,496  6/1971  Chupp .................... 71/118

FOREIGN PATENT DOCUMENTS 779917  3/1968  Canada .
753918  6/1975  South Africa .

*Primary Examiner*—Catherine L. Mills
*Attorney, Agent, or Firm*—William I. Andress

[57] ABSTRACT

The disclosure herein relates to 2-haloacetamides substituted on the amide nitrogen atom with certain specific alkenyl and alkoxyalkyl radicals. These acetamides are useful as herbicides.

12 Claims, No Drawings

HERBICIDAL 2-HALOACETAMIDES

BACKGROUND OF THE INVENTION

1. Field of the Invention

The invention herein pertains to the field of herbicides. More particularly, the field of this invention pertains to the use of 2-haloacetamides as herbicides.

2. Description of the Prior Art

It is known in the prior art to use various 2-haloacetamides as herbicides, either individually or in combination with other herbicides.

Among herbicidal compounds of the prior art are those acetamides having in varying arrangements substitutions of alkyl, cycloalkyl, alkenyl, cycloalkenyl, alkoxy, halogen, aryl, etc. groups, all of which may be further substituted with other radicals.

Illustrative of the 2-haloacetamides of the prior art and of those most closely related in structure to the 2-haloacetamides disclosed and claimed herein to the inventor's knowledge are those disclosed in U.S. Pat. Nos. 3,574,746, 3,586,496, Canadian Pat. No. 779,917 (related in part to U.S. Pat. No. 3,287,106) and South African Pat. No. 753,918. Among the numerous substituents that may be substituted on the amide nitrogen atom are an alkenyl radical ('917, '106 and '918 patents) or a cycloalkenyl radical ('746 and '496 patents) and as a second substituent on the amide nitrogen an alkoxyalkyl radical. Thus, the relevant compounds exemplified in the '746 and '496 U.S. patents are characterized by the simultaneous presence of alkoxyethyl and cycloalkenyl radicals on the amide nitrogen atom. The relevant compounds of said '917 Canadian ('106 U.S.) patent are characterized by the simultaneous presence of alkoxymethyl and alkenyl radicals on the nitrogen atom; this reference does not exemplify any alkenyl radicals having olefinic unsaturation on the carbon atom attached to the amide nitrogen atom, i.e., 2-haloactenamides. Still more particularly, the relevant compounds of said '918 South African patent are characterized by alkoxyethyl and alken-1-yl radicals simultaneously present on the amide nitrogen atom.

As will be apparent from the many combinations and permutations of radicals which may be included on the amide nitrogen, none of the prior art compounds including those most closely related in structure to the invention compounds, include 2-haloacetenamides which may be substituted simultaneously on the amide nitrogen atom with the particular combinations of substituted alkenyl and alkoxyalkyl radicals disclosed and claimed herein, the characteristic and distinguishing features of which are the simultaneous presence on the amide nitrogen atom of an alkoxyalkyl radical and an alkenyl radical substituted with aromatic or heterocyclic radical.

SUMMARY OF THE INVENTION

The present invention relates to herbicidally active compounds, herbicidal compositions containing these compounds and herbicidal method of use of said compositions in agricultural crops, e.g., in dicotyledonous crops such as sugarbeets and soybeans and in monocotyledonous crops such as wheat, sorghum and rice.

The herbicidal compounds of this invention are characterized by the formula

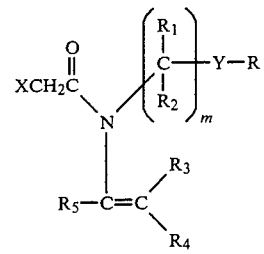

wherein
X is chlorine, bromine or iodine;
y is O, $S(O)_a$ or $N(R_6)_b$
$R_1$, $R_2$ and $R_6$ are independently hydrogen or $C_{1-6}$ alkyl;
$R_3$, $R_4$ and $R_5$ are independently an $R_1$ member, a $C_{6-10}$ aryl or aralkyl radical or a saturated or unsaturated heterocyclyl or heterocyclalkyl radical containing up to 7 ring members of which 1-3 may be any of said Y members or said $R_3$, $R_4$ and $R_5$ members may be substituted with one or more alkyl, alkylthio, alkoxy, polyalkoxy, alkoxyalkyl, halogen, nitro, cyano, trifluoro, hydroxy, amino, mono- or diloweralkyl amino groups; or $R_3$ and $R_4$ may be combined to form a $C_{4-6}$ alkylene radical; provided that not more than two of said $R_3$, $R_4$ and $R_5$ members can be an $R_1$ member;
R is a non-hydrogen $R_3$ member, $C_{1-10}$ alkyl, alkoxyalkyl, polyalkoxyalkyl or acyl, $C_{2-10}$ alkenyl or alkynyl, $C_{3-7}$ cycloalkyl or cycloalkylalkyl, $C_{5-7}$ cycloalkenyl or cycloalkadienyl; provided that when Y is $N(R_6)_b$ and b is 1, R must be and $R_6$ can further be $C_{1-10}$ aryl, haloacyl or sulfonyl;
a is 0, 1 or 2,
b is 0 or 1 and
m is 2, 3 or 4.

Preferred compounds according to this invention are those wherein X is chlorine, $R_1$ and $R_2$ are hydrogen, m is 2, Y is O and R is $C_{1-10}$ lower alkyl.

Preferred species of this invention are:
N-(2-methoxyethyl)-N-(1-phenyl-2-methyl-1-propen-2-yl)-2-chloroacetamide and
N-(2-methoxyethyl)-N-[1-(4-chlorophenyl)-1-propen-1-yl]-2-chloroacetamide).

The above compounds are used singly or in combination as the active ingredient(s) in herbicidal compositions to control undesirable vegetation in important crops.

DESCRIPTION OF PREFERRED EMBODIMENTS

The compounds according to this invention are suitably prepared by reacting the appropriate imine of amine with a haloacylating agent. The starting imine or amine is suitably prepared by reacting the appropriately-substituted ketone with the appropriately-substituted amine.

In specific working embodiments, the preparation of exemplary compounds of this invention will be described in Examples 1-3 below; the same general procedure was followed in order to prepare the compounds of Examples 4-9, but substituting the appropriate starting materials, solvents, reaction conditions, etc., require to obtain the designated product of each example.

EXAMPLE 1

Part (A) of this example describes the preparation of the imine raw material used in Part (B) to prepare the final product.

A. 2-Methoxyethylamine (0.12 mol) and 2-acetylfuran (0.1 mol) were mixed in benzene (70 ml) and heated at reflux temperatures under a Dean and Stark trap for about 24 hours until no more water was given off. The solvent was then stripped and residue vacuum distilled yielding 12.1 gm of pale yellow liquid, b.p. 80° C. at 0.4 mm Hg. identified as N-(methoxyethyl)-1-furyl-1-ethylimine.

B. A mixture of the imine prepared above (0.05 mol) in 30 ml of toluene and chloroacetyl chloride (0.055 mol) in 40 ml of toluene were mixed at 0°–5° C. and stirred for 1.5 hours at room temperature. Triethyl amine (0.06 mol) was added and the mixture stirred an additional 3.0 hours. Water was added and the layers separated; the organic layer was dried over MgSO$_4$ and evaporated. The residual oil was vacuum distilled to yield 2.8 gm of a brown oil product, b.p. 155°–158° C./0.6 mm Hg.

| Anal. for C$_{11}$H$_{14}$ClNO$_3$ (%): | | |
|---|---|---|
| Element | Theory | Found |
| C | 54.22 | 54.50 |
| H | 5.79 | 5.76 |
| N | 5.75 | 5.69 |
| Cl | 14.55 | 14.58 |

The product was identified as N-(2-methoxyethyl)-N-(1-furyl-1-ethylene)-2-chloroacetamide.

EXAMPLE 2

A modification of the general procedure in Part (A) of Example 1 was followed to prepare the imine starting material of this example. In this process a catalyst was used to prepare the imine.

Isobutyrophenone (0.1 mol) and N-(2-methoxyethyl)amine (0.4 mol) in toluene (100 ml) was cooled to 0°–5° C. and titanium tetrachloride (0.05 mol) in toluene (100 ml) was added dropwise with stirring. The reaction mixture was allowed to come to room temperature then refluxed for 8.0 hours. Petroleum ether (500 ml) was then added and the inorganic material removed by filtration. The filtrate was vacuum stripped and the residue distilled to yield an oil, b.p. 88° C./0.4 mm Hg.

| Anal. for C$_{13}$H$_{19}$ClNO (%): | | |
|---|---|---|
| Element | Theory | Found |
| C | 76.06 | 76.02 |
| H | 9.33 | 9.33 |
| N | 8.62 | 8.61 |

The product was identified as N-(2-methoxyethyl)-1-phenyl-2-methylpropylimine.

A mixture of 8.2 gm (0.04 mol) of the above imine in 20 ml of toluene was added to chloroacetyl chloride (0.045 mol) in 50 ml of toluene; then heated at reflux for 7.0 hours. The solvent was stripped and the residual oil redistilled under vacuum to give 11.1 gm (95% yield) of a yellow oil, b.p. 177° at 0.4 mm Hg.

| Anal. for C$_{15}$H$_{20}$ClNO$_2$ (%): | | |
|---|---|---|
| Element | Theory | Found |
| C | 63.94 | 63.73 |
| H | 7.15 | 7.15 |
| N | 4.97 | 4.93 |
| Cl | 12.58 | 12.57 |

The product was identified as N-(2-methoxyethyl)-N-(1-phenyl-2-methylpropen-1-yl)-2-chloroacetamide.

EXAMPLE 3

A mixture of N-(2-methoxyethyl)-1-benzyl-1-ethylimine, 9.6 gm (0.05 mol), prepared similarly as in Part (A) of Example 1, in 40 ml of toluene were mixed with chloroacetyl chloride (0.055 mol) in 40 ml of toluene; this mixture was heated at reflux for 6 hours, the solvent stripped and product distilled in vacuo to yield 8.4 g of amber oil, b.p. 185°/0.6 mm Hg.

| Anal. for C$_{14}$H$_{18}$ClNO$_2$ (%): | | |
|---|---|---|
| Element | Theory | Found |
| C | 62.80 | 62.47 |
| H | 6.78 | 6.63 |
| N | 5.23 | 5.16 |
| Cl | 13.24 | 13.05 |

The product was identified as N-(2-methoxyethyl)-N-(1-phenyl-1-propen-2-yl)-2-chloroacetamide.

EXAMPLES 4–9

Following substantially the same procedures described in the preceding examples, but substituting the appropriate raw materials, reaction conditions, etc., the compounds of Examples 4–9 were prepared; the compounds are identified in Table I with certain physical properties.

TABLE I

| Ex. No. | Compound | Empirical Formula | B.P. °C. (mm Hg.) | Element | Analysis Calculated | Found |
|---|---|---|---|---|---|---|
| 4 | N—(methoxyethyl)-N—(-1-ethyl-2-benzyl-1-propen-1-yl)-2-chloroacetamide | C$_{17}$H$_{24}$ClNO$_2$ | 184–190 (0.7) | C | 65.90 | 64.90 |
| | | | | H | 7.81 | 7.55 |
| | | | | N | 4.52 | 4.75 |
| | | | | Cl | 11.44 | 11.90 |
| 5 | N—(2-methoxyethyl)-N—(1-phenyl-1-buten-1-yl)-2-chloroacetamide | C$_{15}$H$_{20}$ClNO$_2$ | 175–177 (0.4) | C | 63.94 | 63.75 |
| | | | | H | 7.15 | 7.19 |
| | | | | N | 4.97 | 4.95 |
| | | | | Cl | 12.58 | 12.67 |
| 6 | N—(2-methoxyethyl)-N—[1-(4-chlorophenyl)-1-propen-1-yl]-2-chloroacetamide | C$_{14}$H$_7$Cl$_2$NO$_2$ | 184–186 (0.5) | C | 55.64 | 55.49 |
| | | | | H | 5.67 | 5.66 |
| | | | | N | 4.63 | 4.60 |
| | | | | Cl | 23.46 | 23.36 |

TABLE I-continued

| Ex. No. | Compound | Empirical Formula | B.P. °C. (mm Hg.) | Element | Analysis Calculated | Found |
|---|---|---|---|---|---|---|
| 7 | N—(2-methoxyethyl)-N—(1-phenyl-1-propen-1-yl)-2-chloroacetamide | $C_{14}H_{18}ClNO_2$ | 164–165 (0.5) | C<br>H<br>N<br>Cl | 62.80<br>6.78<br>5.23<br>13.24 | 62.77<br>6.79<br>5.22<br>13.23 |
| 8 | N—(2-methoxyethyl)-N—(1-(4-fluorophenyl)-1-propen-1-yl)-2-chloro-acetamide | $C_{14}H_{17}ClFNO_2$ | 158–161 (0.5) | C<br>H<br>N<br>Cl | 58.85<br>6.00<br>4.90<br>12.41 | 58.78<br>6.00<br>4.88<br>12.41 |
| 9 | N—(2-methoxyethyl)-N—[1-(o-tolyl)-1-propen-1-yl]-2-chloroacetamide | $C_{15}H_{20}ClNO_2$ | 162–166 (0.3–0.4) | C<br>H<br>N<br>Cl | 63.49<br>7.15<br>4.97<br>12.58 | 63.33<br>7.16<br>4.80<br>12.28 |

As noted above, the compounds of this invention have been found to be effective as herbicides, particularly as preemergence herbicides, although post-emergence activity has also been shown. Tables II and III summarize results of tests conducted to determine the pre-emergent herbicidal activity of the compounds of this invention.

The pre-emergent tests are conducted as follows:

A good grade of top soil is placed in aluminum pans and compacted to a depth of three-eights to one-half inch from the top of the pan. On the top of the soil is placed a predetermined number of seeds or vegetative propagules of various plant species. The soil required to level fill the pans after seeding or adding vegetative propagules is weighed into a pan. A known amount of the active ingredient applied in a solvent or as a wettable powder suspension and the soil are thoroughly mixed, and used as a cover layer for prepared pans. After treatment, the pans are moved into a greenhouse bench where they are watered from below as needed to give adequate moisture for germination and growth.

Approximately 2–3 weeks after seeding and treating, the plants are observed and the results recorded. Table II below summarizes such results. The herbicidal rating is obtained by means of a fixed scale based on the percent injury of each plant species. The ratings are defined as follows:

| % Control | Rating |
|---|---|
| 0–24 | 0 |
| 25–49 | 1 |
| 50–74 | 2 |
| 75–100 | 3 |

The plant species utilized in one set of tests, the data for which are shown in Table 2, are identified by letter in accordance with the following legend:

TABLE II

| Compound of Example No. | Kg/ha | \multicolumn{11}{c}{Pre-Emergent Plant Species} |
|---|---|---|---|---|---|---|---|---|---|---|---|---|

| Compound of Example No. | Kg/ha | A | B | C | D | E | F | G | H | I | J | K |
|---|---|---|---|---|---|---|---|---|---|---|---|---|
| 1 | 11.2 | 0 | 0 | 0 | — | 0 | 0 | 0 | 0 | 0 | 0 | 3 |
|   | 5.6 | 0 | 0 | 0 | — | 0 | 0 | 0 | 0 | 0 | 0 | 3 |
| 2 | 11.2 | 3 | 1 | 3 | 3 | 3 | 3 | 3 | 3 | 2 | 3 | 3 |
|   | 5.6 | 3 | 0 | 2 | 2 | 3 | 3 | 3 | 3 | 0 | 3 | 3 |
| 3 | 11.2 | 0 | 0 | 0 | 0 | 3 | 3 | 3 | 0 | 0 | 1 | 3 |
|   | 5.6 | 0 | 0 | 0 | 0 | 1 | 1 | 1 | 3 | 0 | 0 | 3 |
| 4 | 11.2 | 0 | 0 | 0 | 0 | 3 | 2 | 3 | 1 | 1 | 3 | 3 |
|   | 5.6 | 1 | 0 | 1 | 5 | 3 | 1 | 1 | 0 | 0 | 0 | 3 |
| 5 | 11.2 | 3 | 0 | 0 | 0 | 3 | 3 | 3 | 0 | 0 | 3 | 3 |
|   | 5.6 | 3 | 0 | 1 | 0 | 3 | 3 | 2 | 0 | 0 | 3 | 3 |
| 6 | 11.2 | 0 | 0 | 0 | 0 | 2 | 0 | 3 | 1 | 0 | 3 | 3 |
|   | 5.6 | 0 | 0 | 0 | 0 | 1 | 0 | 3 | 1 | 0 | 2 | 3 |
| 7 | 11.2 | 0 | 0 | 1 | 0 | 2 | 1 | 2 | 3 | 0 | 3 | 3 |
|   | 5.6 | 0 | 0 | 0 | 1 | 3 | 1 | 3 | 0 | 2 | 3 | 3 |
| 8 | 11.2 | 0 | 0 | 0 | 0 | 2 | 1 | 3 | 2 | 0 | 3 | 3 |
|   | 5.6 | 0 | 0 | 0 | 0 | 2 | 0 | 3 | 1 | 0 | 1 | 3 |
| 9 | 11.2 | 1 | 0 | 1 | 1 | 3 | 3 | 1 | 2 | 0 | 3 | 3 |
|   | 5.6 | 0 | 0 | 0 | 1 | 2 | 2 | 3 | 0 | 0 | 3 | 3 |

A Canada Thistle
B Cocklebur
C Velvetleaf
D Morningglory
E Lambsquarters
F Smartweed
G Yellow Nutsedge
H Quackgrass
I Johnsongrass
J Downy Brome
K Barnyardgrass The compounds were further tested by utilizing the above procedure on the following plant species:

| L | Soybean | R | Hemp Sesbania |
|---|---|---|---|
| M | Sugarbeet | E | Lambsquarters |
| N | Wheat | F | Smartweed |
| O | Rice | C | Velvetleaf |
| P | Sorghum | J | Downy brome |
| B | Cocklebur | | |
| Q | Wild Buckwheat | S | Panicum |
| D | Morningglory | K | Barnyardgrass |
| | | T | Crabgrass |

The results are summarized in Table III.

TABLE III

| Compound of Example No. | Kg/ha | L | M | N | O | P | B | Q | D | R | E | F | C | J | S | K | T |
|---|---|---|---|---|---|---|---|---|---|---|---|---|---|---|---|---|---|
| 1 | 5.6 | 0 | 1 | 0 | 1 | 0 | 0 | 0 | 0 | 1 | 3 | 0 | 0 | 1 | 3 | 3 | 3 |
|   | 1.12 | 0 | 0 | 0 | 0 | 0 | — | 0 | — | 0 | 3 | 1 | 0 | 0 | 2 | 2 | 2 |
|   | 0.28 | 1 | 0 | 0 | 0 | 0 | — | 0 | 0 | 0 | 0 | 0 | 0 | 0 | 0 | 2 | 1 |
| 2 | 5.6 | 1 | 2 | 3 | 3 | 3 | — | 2 | 3 | 2 | 3 | 3 | 3 | 3 | 3 | 3 | 3 |
|   | 1.12 | 0 | 1 | 1 | 3 | 3 | 2 | 1 | 2 | 1 | 3 | 3 | 1 | 2 | 3 | 3 | 3 |

TABLE III-continued

| Compound of Example No. | Kg/ha | Pre-Emergent Plant Species | | | | | | | | | | | | | | |
|---|---|---|---|---|---|---|---|---|---|---|---|---|---|---|---|---|
| | | L | M | N | O | P | B | Q | D | R | E | F | C | J | S | K | T |
| | 0.28 | 0 | 1 | 1 | 3 | 2 | — | 0 | 1 | 1 | 3 | 3 | 0 | 0 | 3 | 3 | 3 |
| | 0.056 | 0 | 0 | 0 | 2 | 0 | — | 0 | 1 | 0 | 3 | 2 | 0 | 0 | 2 | 3 | 3 |
| | 0.0112 | 0 | 0 | 0 | 2 | 0 | — | 0 | 0 | 1 | 1 | 1 | 0 | 0 | 1 | 3 | 2 |
| 3 | 5.6 | 0 | 1 | 0 | 2 | 2 | 0 | 0 | 0 | 0 | 3 | 3 | 0 | 2 | 3 | 3 | 3 |
| | 1.12 | 0 | 1 | 1 | 0 | 0 | — | 0 | 0 | 0 | 2 | 0 | 0 | 0 | 0 | 3 | 3 |
| | 0.28 | 0 | 0 | 0 | 0 | 0 | — | 0 | 0 | — | 0 | 0 | 0 | 0 | 0 | 3 | 2 |
| | 0.056 | 0 | — | 0 | 0 | 0 | — | 0 | 0 | 0 | 0 | 0 | 0 | 0 | 0 | 3 | 0 |
| 4 | 5.6 | 0 | 1 | 3 | 3 | 3 | — | 0 | 1 | 1 | 3 | 2 | 0 | 0 | 3 | 3 | 3 |
| | 1.12 | 0 | 1 | 0 | 2 | 0 | 0 | 0 | 0 | 0 | 0 | 0 | 0 | 0 | 2 | 3 | 3 |
| | 0.28 | 2 | 1 | 0 | 1 | 0 | — | 0 | — | 0 | 3 | 1 | 0 | 0 | 0 | 3 | 2 |
| 5 | 5.6 | 0 | 1 | 1 | 3 | 3 | 1 | 0 | 0 | 0 | 3 | 1 | 0 | 3 | 3 | 3 | 3 |
| | 1.12 | 0 | 1 | 0 | 2 | 1 | 0 | 0 | 0 | 0 | 2 | 0 | 0 | 3 | 3 | 3 | 3 |
| | 0.28 | 1 | 0 | 0 | 2 | 0 | 0 | 0 | 1 | 1 | 0 | 0 | 0 | 0 | 3 | 3 | 3 |
| | 0.056 | 0 | 0 | 0 | 0 | 0 | 0 | 0 | 0 | 0 | 0 | 0 | 0 | 0 | 1 | 2 | 1 |
| | 0.0112 | 0 | 0 | 0 | 0 | 0 | 0 | 0 | 0 | 0 | 0 | 0 | 0 | 0 | 0 | 0 | 0 |
| 6 | 5.6 | 0 | 0 | 0 | 2 | 2 | 3 | 0 | 0 | 3 | 3 | 3 | 0 | 3 | 3 | 3 | 3 |
| | 1.12 | 0 | 0 | 0 | 1 | 0 | 0 | 0 | 1 | 0 | 0 | 0 | 0 | 0 | 2 | 3 | 2 |
| | 0.28 | 0 | 0 | 0 | 0 | 0 | 0 | 0 | 0 | 1 | 0 | 1 | 0 | 0 | 0 | 3 | 1 |
| | 0.056 | 0 | 0 | 0 | 0 | 0 | 0 | 0 | 0 | 0 | 0 | 0 | 0 | 0 | 0 | 0 | 1 |
| 7 | 5.6 | 0 | 3 | 3 | 3 | 3 | 3 | 1 | 1 | 3 | 3 | 3 | 0 | 3 | 3 | 3 | 3 |
| | 1.12 | 0 | 0 | 0 | 1 | 0 | 3 | 0 | 0 | 0 | 0 | 1 | 0 | 2 | 3 | 3 | 3 |
| | 0.28 | 0 | 0 | 0 | 1 | 0 | 0 | 0 | 0 | 3 | 0 | 0 | 0 | 0 | 0 | 3 | 2 |
| | 0.056 | 1 | 0 | 0 | 0 | 0 | 3 | 0 | 0 | 3 | 0 | 1 | 0 | 0 | 0 | 1 | 1 |
| | 0.0112 | 0 | 0 | 0 | 0 | 3 | 0 | 0 | 0 | 1 | 1 | 0 | 0 | 0 | 0 | 0 | 0 |
| 8 | 5.6 | 0 | 1 | 0 | 3 | 1 | 0 | 2 | 0 | 0 | 1 | 1 | 0 | 3 | 3 | 3 | 3 |
| | 1.12 | 0 | 0 | 0 | 1 | 0 | 0 | 0 | 0 | 0 | 2 | 1 | 0 | 0 | 3 | 3 | 3 |
| | 0.28 | 0 | 0 | 0 | 1 | 0 | 0 | 0 | 0 | 3 | 0 | 0 | 0 | 0 | 2 | 3 | 2 |
| | 0.056 | 0 | 1 | 0 | 0 | 0 | 0 | 0 | 0 | 3 | 0 | 0 | 0 | 0 | 0 | 2 | 0 |
| 9 | 5.6 | 1 | 1 | 1 | 1 | 1 | 0 | 0 | 0 | 2 | 3 | 2 | 0 | 3 | 3 | 3 | 3 |
| | 1.12 | 0 | 1 | 0 | 0 | 0 | 0 | 0 | 1 | 1 | 1 | 0 | 0 | 3 | 3 | 3 | 3 |
| | 0.28 | 0 | 0 | 0 | 0 | 0 | 0 | 0 | 0 | 1 | 1 | 0 | 0 | 3 | 3 | 3 | 2 |
| | 0.056 | 0 | 0 | 0 | 0 | 0 | 0 | 1 | 0 | 0 | 0 | 0 | 0 | 1 | 1 | 1 | 0 |

EXAMPLES 10-55

Yet other compounds corresponding to the above generic formula and contemplated as within the scope of this invention are shown in Table IV. In the examples, the individual compounds are those whose members are identified by the generic formula.

TABLE IV

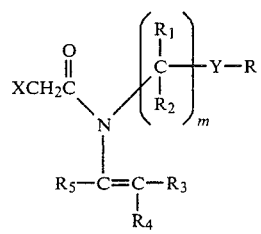

| Cpd. of Ex. No. | X | $R_1$ | $R_2$ | m | Y | R | $R_3$ | $R_4$ | $R_5$ |
|---|---|---|---|---|---|---|---|---|---|
| 10 | Cl | H | H | 2 | O | $C_2H_5$ | $CH_3$ | $CH_3$ |  |
| 11 | Cl | H | H | 2 | O | $C_3H_7$ | $CH_3$ | $CH_3$ |  |
| 12 | Br | H | H | 2 | O | $C_2H_5$ | $CH_3$ | $CH_3$ |  |
| 13 | Br | H | H | 2 | O | n-$C_3H_7$ | $CH_3$ | $CH_3$ |  |
| 14 | Cl | 1-$CH_3$ | H | 2 | O | i-$C_3H_7$ | H | $CH_3$ |  |
| 15 | Cl | 2-$CH_3$ | H | 2 | O | n-$C_4H_9$ | H | $CH_3$ |  |

TABLE IV-continued

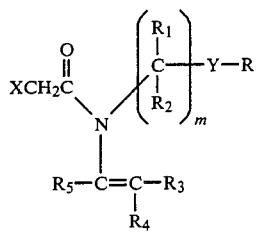

| Cpd. of Ex. No. | X | $R_1$ | $R_2$ | m | Y | R | $R_3$ | $R_4$ | $R_5$ |
|---|---|---|---|---|---|---|---|---|---|
| 16 | Cl | 1,2-di-CH$_3$ | H | 2 | O | n-C$_5$H$_9$ | CH$_3$ | H | 2-methylphenyl |
| 17 | Cl | 1-CH$_3$ | 1-CH$_3$ | 2 | O | allyl | H | H | 2-methylphenyl |
| 18 | Br | H | H | 3 | O | CH$_3$ | CH$_3$ | CH$_3$ | furyl |
| 19 | I | H | H | 2 | O | C$_2$H$_5$ | H | H | phenyl |
| 20 | Cl | H | H | 2 | O | i-C$_3$H$_7$ | H | phenyl | CH$_3$ |
| 21 | Cl | H | H | 2 | S | C$_2$H$_5$ | CH$_3$ | CH$_3$ | phenyl |
| 22 | Cl | H | H | 2 | S | n-C$_3$H$_5$ | CH$_3$ | CH$_3$ | phenyl |
| 23 | Br | H | H | 2 | S | i-C$_3$H$_7$ | CH$_3$ | CH$_3$ | phenyl |
| 24 | Br | 1-CH$_3$ | 1-CH$_3$ | 2 | S | n-C$_4$H$_9$ | H | CH$_3$ | 2-methylphenyl |
| 25 | Cl | H | H | 2 | S | —CH$_2$CH=CH$_2$CH$_3$ | CH$_3$ | CH$_3$ | 2-methoxyphenyl |
| 26 | Cl | H | H | 2 | O | —CH$_2$C≡CH | CH$_3$ | CH$_3$ | phenyl |
| 27 | Cl | H | H | 2 | —NH— | —C(O)—CH$_3$ | CH$_3$ | CH$_3$ | chlorophenyl |
| 28 | Cl | H | H | 2 | —N(CH$_3$)— | —C(O)—CH$_2$CH$_3$ | H | C$_2$H$_5$ | 4-chlorophenyl |
| 29 | Cl | H | H | 2 | O | furyl | CH$_3$ | CH$_3$ | furyl |

TABLE IV-continued $$XCH_2\overset{O}{\underset{\underset{R_5-\overset{|}{C}=\overset{|}{\underset{R_4}{C}}-R_3}{N}}{C}}-\left(\overset{R_1}{\underset{R_2}{C}}\right)_m-Y-R$$

| Cpd. of Ex. No. | X | $R_1$ | $R_2$ | m | Y | R | $R_3$ | $R_4$ | $R_5$ |
|---|---|---|---|---|---|---|---|---|---|
| 30 | Cl | H | H | 2 | O | n-$C_3H_7$ | $CH_3$ | $CH_3$ | tetrahydrofuran-2-yl (S,O ring) |
| 31 | Cl | H | H | 2 | O | i-$C_3H_7$ | $CH_3$ | $CH_3$ | 2-thienyl |
| 32 | Br | 1-$C_2H_5$ | H | 2 | O | n-$C_4H_9$ | $CH_3$ | $CH_3$ | 2-pyridyl |
| 33 | Cl | H | H | 2 | $-\overset{O}{\underset{}{S}}-$ | $CH_3$ | $CH_3$ | $CH_3$ | 2-thienyl |
| 34 | Cl | 1-$CH_3$ | H | 2 | $-\overset{O}{\underset{O}{S}}-$ | $C_2H_5$ | phenyl | $CH_3$ | i-$C_3H_7$ |
| 35 | Cl | H | H | 2 | O | $CH_3$ | 2-furyl | $CH_3$ | $CH_3$ |
| 36 | Br | H | 1-$CH_3$ | 2 | O | —i-$C_3H_7$ | 2-thienyl | $C_2H_5$ | $C_2H_5$ |
| 37 | I | H | H | 2 | O | $CH_3$ | H | $CH_3$ | 2-($OCH_2OCH_3$)phenyl |
| 38 | Cl | H | H | 4 | O | $CH_3$ | $CH_3$ | $CH_3$ | phenyl |
| 39 | Cl | H | H | 2 | O | allyl | phenyl | H | 2-$NO_2$-phenyl |
| 40 | Cl | H | H | 2 | O | allyl | $CH_3$ | $CH_3$ | 4-$NH_2$-phenyl |
| 41 | Cl | H | H | 2 | O | $CH_3$ | $CH_3$ | $CH_3$ | 4-$N(CH_3)_2$-phenyl |
| 42 | Cl | H | H | 2 | O | $CH_3$ | $CH_3$ | $CH_3$ | 3-$CF_3$-phenyl |

TABLE IV-continued

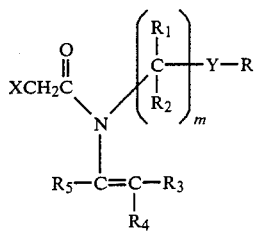

| Cpd. of Ex. No. | X | $R_1$ | $R_2$ | m | Y | R | $R_3$ | $R_4$ | $R_5$ |
|---|---|---|---|---|---|---|---|---|---|
| 43 | Cl | H | H | 2 | O | $CH_3$ | $CH_3$ | $CH_3$ | 4-CN-phenyl |
| 44 | Cl | H | H | 2 | O | $CH_3$ | $CH_3$ | $CH_3$ | 2-OH-phenyl |
| 45 | Cl | H | H | 2 | O | $CH_3$ | $n$-$C_3H_7$ | 2-methyl-2,3-dihydrofuran-2-yl | $CH_3$ |
| 46 | Cl | H | H | 2 | O | $C_2H_5$ | $CH_3$ | 1,2,4-triazol-3-yl | $CH_3$ |
| 47 | Cl | H | H | 2 | O | phenyl | H | $CH_3$ | phenyl |
| 48 | Cl | H | H | 2 | O | 2-naphthyl | $CH_3$ | $CH_3$ | $-CH_2$-phenyl |
| 49 | Cl | H | H | 2 | O | $-CH_2$-(3-Cl-phenyl) | phenyl | $CH_3$ | $CH_3$ |
| 50 | Cl | H | H | 2 | O | 3-$OCH_3$-phenyl | 3-$OCH_3$-phenyl | $CH_3$ | $CH_3$ |
| 51 | Cl | H | H | 2 | O | $CH_3$ | $CH_3$ | $CH_3$ | 2,2-dimethyl-1,3-dioxolan-4-yl |
| 52 | Br | H | H | 2 | S | $C_2H_5$ | $C_2H_5$ | $C_2H_5$ | 1,3-dioxolan-2-ylmethyl |
| 53 | Cl | 1-$CH_3$ | H | 2 | O | $-CH_2$-N(thiazolyl) | $n$-$C_3H_7$ | $n$-$C_3H_7$ | phenyl |
| 54 | Cl | H | H | 2 | O | 1,3,4-oxadiazol-2-yl | $CH_3$ | $CH_3$ | phenyl |

TABLE IV-continued

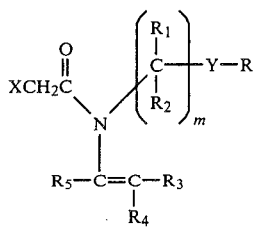

| Cpd. of Ex. No. | X | R₁ | R₂ | m | Y | R | R₃ | R₄ | R₅ |
|---|---|---|---|---|---|---|---|---|---|
| 55 | Cl | H | H | 2 | O | ![N=N ring with C-O-C] | CH₃ | CH₃ | —⟨phenyl⟩ |
| 56 | Cl | H | H | 1 | O | i-C₃H₇ | | (CH₂) | —⟨phenyl⟩ |

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor of anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

In another form of aqueous suspensions, a water-immiscible herbicide is encapsulated to form microencapsulated phase dispersed in an aqueous phase. In one embodiment, minute capsules are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total compositions preferably 480 to 600 g/l. The microencapsulation process referred to here is described in more detail in the assignee's copending U.S. Ser. No. 23,566 filed Mar. 26, 1979.

Concentrates are usually solutions of active ingredient in water-immiscible or partially water-immiscible solvents together with a surface active agent. Suitable solvents for the active ingredient of this invention include dimethylformide, dimethylsulfoxide, N-methylpyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts preferably from about 3 to 20 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as:

HETEROCYCLIC NITROGEN/SULFUR DERIVATIVES

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a.2',1'-c)-pyrazidiinium salt
5-Bromo-3-isopropyl-6-methyluracil
1,1'-Dimethyl-4,4'-bipyridinium

UREAS

N'-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea

CARBAMATES/THIOLCARBAMATES

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
Ethyl N,N-dipropylthiolcarbamate
S-propyl dipropylthiolcarbamate

ACETAMIDES/ACETANILIDES/ANILINES/AMIDES

2-Chloro-N,N-diallylacetamide
N,N-dimethyl-2,2-diphenylacetamide
N-(2,4-dimethyl-5-[[(trifluoromethyl)sulfonyl]amino]-phenyl)acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
$\alpha,\alpha,\alpha$-Trifluoro-2,6-dinitro-N,N-dipropyl-p-toluidine
N-(1,1-dimethylpropynyl)-3,5-dichlorobenzamide

ACIDS/ESTERS/ALCOHOLS 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its $C_{1-6}$ monoalkyl amine and alkaline metal salts and combinations thereof

ETHERS 2,4-Dichlorophenyl-4-nitrophenyl ether
2-Chloro-$\alpha,\alpha,\alpha$-trifluoro-p-tolyl-3-ethoxy-4-nitrodiphenyl ether

MISCELLANEOUS 2,6-Dichlorobenzonitrile
Monosodium acid methanearsonate
Disodium methanearsonate Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

|  |  | Weight Percent |
|---|---|---|
| I. Emulsifiable Concentrates |  |  |
| A. | Compound of Example No. 1 | 50.0 |
|  | Calcium dodecylbenzene sulfonate/polyoxyethylene ethers blend (e.g., Atlox ® 3437F and Atlox 3438F) | 5.0 |
|  | Monochlorobenzene | 45.0 |
|  |  | 100.00 |
| B. | Compound of Example No. 2 | 85.0 |
|  | Calcium dodecyl sulfonate/alkylaryl polyether alcohol blend | 4.0 |
|  | C9 aromatic hydrocarbons solvent | 11.0 |
|  |  | 100.00 |
| C. | Compound of Example No. 3 | 5.0 |
|  | Calcium dodecylbenzene sulfonate/poly- | 1.0 |

| | Weight Percent |
|---|---|
| oxyethylene ethers blend (e.g., Atlox 3437F) | |
| Xylene | 94.0 |
| | 100.00 |
| II. Liquid Concentrates | |
| A. Compound of Example No. 4 | 10.0 |
| Xylene | 90.0 |
| | 100.00 |
| B. Compound of Example No. 5 | 85.0 |
| Dimethyl sulfoxide | 15.0 |
| | 100.00 |
| C. Compound of Example No. 6 | 50.0 |
| N—methylpyrrolidone | 50.0 |
| | 100.00 |
| D. Compound of Example No. 7 | 5.0 |
| Ethoxylated castor oil | 20.0 |
| Rhodamine B | .5 |
| Dimethyl fomamide | 74.5 |
| | 100.00 |
| III. Wettable Powders | |
| A. Compound of Example No. 8 | 25.0 |
| Sodium lignosulfonate | 3.0 |
| Sodium N—methyl-N—oleyl-taurate | 1.0 |
| Amorphous silica (synthetic) | 71.0 |
| | 100.00 |
| B. Compound of Example No. 9 | 80.0 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 1 | 10.0 |
| Sodium lignosulfonate | 3.0 |
| Sodium N—methyl-N—oleyl-taurate | 1.0 |
| Kaolinite clay | 86.0 |
| | 100.00 |
| IV. Dusts | |
| A. Compound of Example No. 2 | 2.0 |
| Attapulgite | 98.0 |
| | 100.00 |
| B. Compound of Example No. 3 | 60.0 |
| Montmorillonite | 40.0 |
| | 100.00 |
| C. Compound of Example No. 4 | 30.0 |
| Bentonite | 70.0 |
| | 100.00 |
| D. Compound of Example No. 5 | 1.0 |
| Diatomaceous earth | 99.0 |
| | 100.00 |
| V. Granules | |
| A. Compound of Example No. 6 | 15.0 |
| Granular attapulgite (20/40 mesh) | 85.0 |
| | 100.00 |
| B. Compound of Example No. 7 | 30.0 |
| Diatomaceous earth (20/40) | 70.0 |
| | 100.00 |
| C. Compound of Example No. 8 | 0.5 |
| Bentonite (20/40) | 99.5 |
| | 100.00 |
| D. Compound of Example No. 9 | 5.0 |
| Pyrophyllite (20/40) | 95.0 |
| | 100.00 |

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective preemergence application to the plants or to the soil a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. One skilled in the art can readily determine from this specification, including the above example, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

I claim:

1. Compounds having the formula

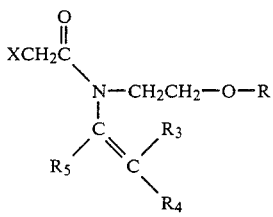

wherein
X is chlorine, bromine or iodine;
R is $C_{1-10}$ lower alkyl;
$R_3$ and $R_4$ are hydrogen, $C_{1-6}$ alkyl, benzyl or phenyl; and
$R_5$ is $C_{1-6}$ lower alkyl, tetrahydrofuryl, phenyl or phenyl substituted with lower alkyl or halogen; provided that not more than two of $R_3$, $R_4$ and $R_5$ members are hydrogen or alkyl.

2. Compounds according to claim 1 wherein X is chlorine and R is $C_{1-10}$ lower alkyl.

3. Compound according to claim 2 which is N-(2-methoxyethyl)-N-(1-phenyl-2-methyl-1-propen-1-yl)-2-chloroacetamide.

4. Compound according to claim 2 which is N-(2-methoxyethl)-N-[1-(4-chlorophenyl)-1-propen-1-yl]-2-chloroacetamide.

5. Herbicidal compositions comprising an adjuvant and a herbicidally effective amount of a compound having the formula

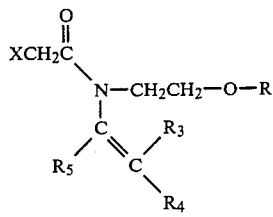

wherein
X is chlorine, bromine or iodine;
R is $C_{1-10}$ lower alkyl;
$R_3$ and $R_4$ are hydrogen, $C_{1-6}$ alkyl, benzyl or phenyl; and
$R_5$ is $C_{1-6}$ lower alkyl, tetrahydrofuryl, phenyl or phenyl substituted with lower alkyl or halogen; provided that not more than two of $R_3$, $R_4$ and $R_5$ members are hydrogen or alkyl.

6. Composition according to claim 5 wherein in said compound X is chlorine and R is $C_{1-10}$ lower alkyl.

7. Composition according to claim 6 wherein said compound is N-(2-methoxyethyl)-N-(1-phenyl-2-methyl-1-propen-1-yl)-2-chloroacetamide.

8. Composition according to claim 6 wherein said compound is N-(2-methoxyethyl)-N-[1-(4-chlorophenyl)-1-propen-1-yl]-2-chloroacetamide.

9. Method for combatting undesirable plants in crops which comprises applying to the locus thereof a herbicidally effective amount of a compound having the formula

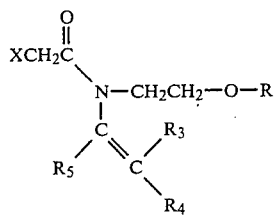

wherein
X is chlorine, bromine or iodine;
R is $C_{1-10}$ lower alkyl;
$R_3$ and $R_4$ are hydrogen, $C_{1-6}$ alkyl, benzyl or phenyl; and
$R_5$ is $C_{1-6}$ lower alkyl, tetrahydrofuryl, phenyl or phenyl substituted with lower alkyl or halogen, provided that not more than two of $R_3$, $R_4$ and $R_5$ members are hydrogen or alkyl.

10. Method according to claim 9 wherein in said compound X is chlorine and R is $C_{1-10}$ lower alkyl.

11. Method according to claim 10 wherein said compound is N-(2-methoxyethyl)-N-(1-phenyl-2-methyl-1-propen-1-yl)-2-chloroacetamide.

12. Method according to claim 10 wherein said compound is N-(2-methoxyethyl)-N-[1-(4-chlorophenyl)-1-propen-1-yl]-2-chloroacetamide.

* * * * *